(12) United States Patent
Evans et al.

(10) Patent No.: US 7,399,307 B2
(45) Date of Patent: Jul. 15, 2008

(54) APPARATUS AND METHOD FOR REMOVING OCCLUSIVE MATERIAL WITHIN BLOOD VESSELS

(75) Inventors: Michael A. Evans, Palo Alto, CA (US); Denise Demarais, Los Gatos, CA (US); Alexander Khairkhahan, Palo Alto, CA (US); Dino Decicco, San Jose, CA (US)

(73) Assignee: Bacchus Vascular, Inc., Santa Clara, CA (US)

( * ) Notice: Subject to any disclaimer, the term of this patent is extended or adjusted under 35 U.S.C. 154(b) by 88 days.

(21) Appl. No.: 10/438,266

(22) Filed: May 13, 2003

(65) Prior Publication Data

US 2004/0006306 A1 Jan. 8, 2004

Related U.S. Application Data

(60) Provisional application No. 60/380,596, filed on May 14, 2002.

(51) Int. Cl.
*A61M 29/00* (2006.01)
*A61B 17/22* (2006.01)

(52) U.S. Cl. ............... 606/194; 606/159

(58) Field of Classification Search ......... 606/191–194; 623/1.11–1.22
See application file for complete search history.

(56) References Cited

U.S. PATENT DOCUMENTS 4,762,129 A 8/1988 Bonzel
5,061,273 A 10/1991 Yock
5,158,564 A 10/1992 Schnepp-Pesch et al.
5,395,332 A 3/1995 Ressemann et al.
5,462,529 A * 10/1995 Simpson et al. ........ 604/101.04
5,868,708 A 2/1999 Hart et al.
5,921,958 A * 7/1999 Ressemann et al. ...... 604/96.01
6,309,412 B1 10/2001 Lau et al.
2003/0191436 A1* 10/2003 Horvers ................. 604/103.04

FOREIGN PATENT DOCUMENTS

| WO | WO 96/01591 A1 | 1/1996 |
| WO | WO 99/22673 A1 | 5/1999 |
| WO | WO 99/23976 A1 | 5/1999 |
| WO | WO 01/15629 A1 | 3/2001 |
| WO | WO 01/21100 A1 | 3/2001 |
| WO | WO 01/54754 A1 | 8/2001 |

* cited by examiner

*Primary Examiner*—Vy Q. Bui
(74) *Attorney, Agent, or Firm*—Townsend and Townsend and Crew LLP

(57) ABSTRACT

An apparatus for treating an occlusive region of a blood vessel includes a catheter including a first lumen extending from an end port to a first side port, and a second lumen extending from a proximal end of the catheter to a second side port. A balloon is mounted on the catheter between the first and second side ports. During use, a guidewire is placed into an occlusive region, and the guidewire is backloaded through the first and second lumens. The catheter is advanced over the guidewire, and the balloon is expanded to isolate the occlusive region. The guidewire is removed, and an agitator is advanced through the second lumen. After the agitator is agitated to dislodge occlusive material from the occlusive region, the agitator is removed, and the loose occlusive material is aspirated via the second side port.

19 Claims, 5 Drawing Sheets

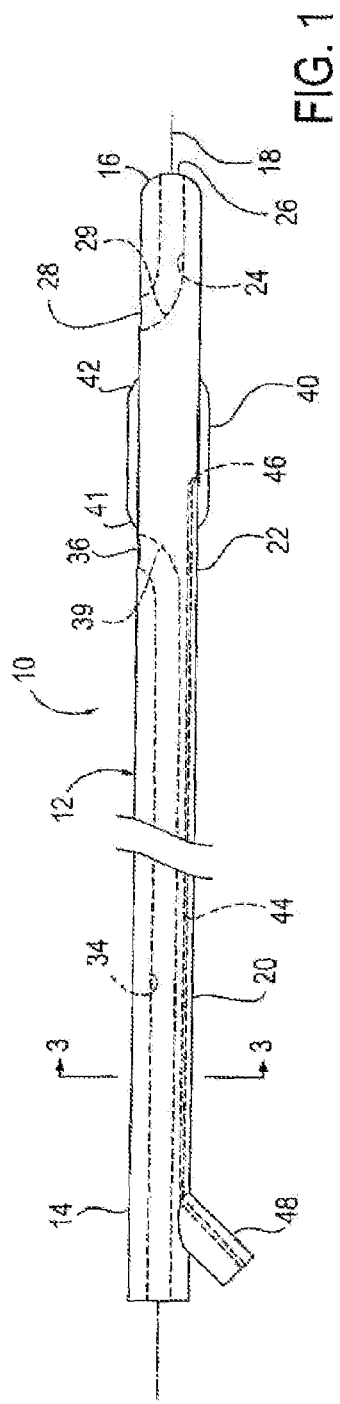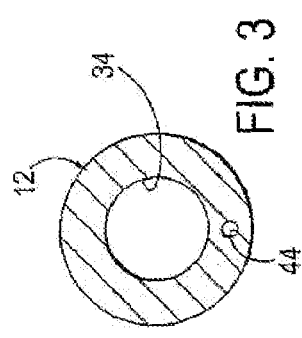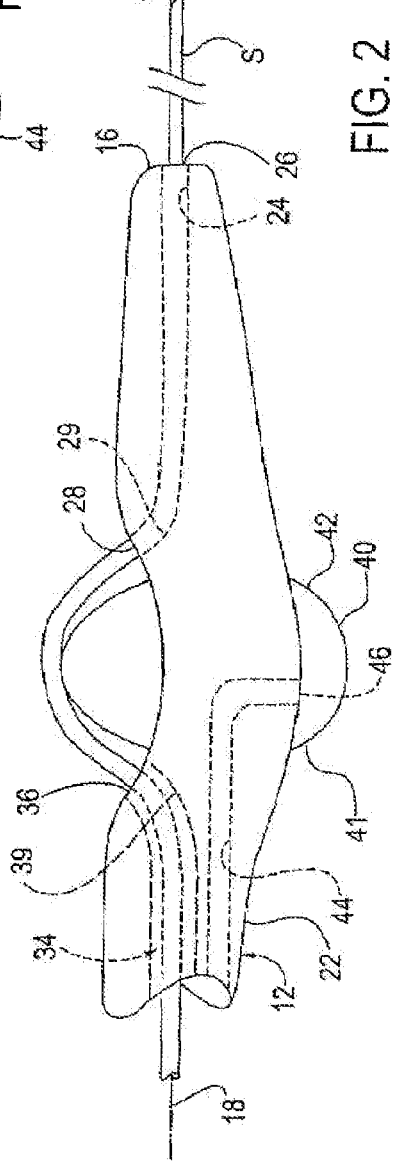

APPARATUS AND METHOD FOR REMOVING OCCLUSIVE MATERIAL WITHIN BLOOD VESSELS

CROSS-REFERENCES TO RELATED APPLICATIONS

The present application is a non-provisional of U.S. Patent Application Ser. No. 60/380,596, filed May 14, 2002, the full disclosure of which is incorporated herein by reference.

BACKGROUND OF THE INVENTION

Field of the Invention

The present invention relates generally to apparatus and methods for treating a blood vessel or other body lumen, and more particularly to apparatus and methods for disrupting, dissolving, and/or otherwise removing occlusive material, such as thrombus, from a treatment site, e.g., an occlusion within a blood vessel.

A number of endovascular procedures are known for treating patients with atherosclerotic disease and the like, e.g., to treat stenoses, occlusions, lesions, or other regions within a patient's blood vessels, such as within the coronary, carotid, or cerebral arteries. For example, an angioplasty procedure may be used to dilate a stenosis, or a thrombectomy or atherectomy may be performed to open severely occluded regions. A stent or other prosthesis may be implanted to dilate and/or retain patency of a vessel, either alone or in conjunction with these procedures.

During such procedures, multiple balloon catheters may be advanced successively over a guidewire already placed within a treatment site. For example, during angioplasty or stent delivery, catheters with successively larger balloons may be advanced into a stenosis to dilate the stenosis to a desired size. To facilitate replacing one catheter with another, "rapid exchange" catheters have been suggested that include a relatively short lumen that extends through the balloon on the distal end of the catheter. With such catheters, a guidewire need only be backloaded through this short lumen, rather than through a lumen extending the entire length of the catheter, before introducing the catheter into a patient's vasculature. This may substantially reduce the time required to exchange catheters during a procedure. U.S. Pat. No. 4,762,129 to Bonzel and U.S. Pat. No. 5,063,273 to Yock disclose exemplary catheters of this type.

In addition, procedures have been suggested for disrupting and/or dissolving clots using a catheter having an agitator and/or an ability to deliver a thrombolytic agent. The catheter may be introduced into a target region within a blood vessel and the agitator may be manipulated to engage and/or disrupt a region of clot therein. A thrombolytic agent may be released into the target region where the agitator is treating the clot. In this way, the thrombolytic activity of the agent may be enhanced and the clot may be dissolved or otherwise treated. PCT publication WO 01/54754, published Aug. 8, 2001, discloses apparatus and methods for performing such procedures.

Accordingly, apparatus and methods for disrupting, dissolving, capturing and/or removing particulate material, such as thrombus or occlusive material, within a blood vessel would be considered useful.

BRIEF SUMMARY OF THE INVENTION

The present invention is directed to apparatus and methods for treating a blood vessel or other body lumen, and more particularly to apparatus and methods for disrupting, dissolving, and/or otherwise removing occlusive material, such as thrombus, from a treatment site, e.g., an occlusion within a blood vessel.

In accordance with one aspect of the present invention, an apparatus is provided that includes a tubular member including proximal and distal ends, and a distal portion including a first lumen therein. The first lumen includes an end port at or adjacent the distal end and a first side port located proximally to the end port. The tubular member also includes a second lumen extending from the proximal end to a second side port located proximally to the first side port. An expandable member, e.g., a compliant balloon, is mounted on the tubular member between the first and second side ports.

In an alternative embodiment, the first and second lumens may be a single lumen extending between the proximal and distal ends of the tubular member. A blocker may be secured or otherwise provided within the single lumen between the first and second side ports for dividing the single lumen into the first and second lumens. Preferably, the blocker is substantially permanently secured within the single lumen, e.g., using an adhesive, melting, sonic welding, constricting the wall of the tubular member, and the like.

One or more treatment devices may be used in conjunction with the apparatus. For example, a source of aspiration may be connected to the proximal end of the tubular member, the source of aspiration communicating with the second lumen for creating a vacuum at the second side port. In addition or alternatively, a treatment element may be insertable through the second lumen, e.g., an agitator including a nonlinear portion. The distal portion of the tubular member may include a flexible portion proximal to the expandable member, the nonlinear portion being insertable into the flexible portion for deforming the flexible portion into a nonlinear configuration.

During use, a guidewire may be placed into a target site, e.g., within a blood vessel or other body lumen. For example, the target site may be an occlusive region to be treated within an artery. The guidewire may be backloaded through the first lumen, around the expandable member, and through the second lumen. The distal portion of the tubular member may be advanced over the guidewire to the target site.

The expandable member on the tubular member may be expanded to at least partially isolate the target site. Optionally, a proximal expandable member may be expanded to further isolate the target site. For example, the proximal expandable member may be disposed on the tubular member at a location proximal to the second side port. Alternatively, the proximal expandable member may be carried on a distal portion of an elongate member advanced to the occlusive region.

A treatment element may be advanced into the target site in cooperation with the tubular member, and the target site may be treated. In one embodiment, the guidewire may be removed from the second lumen, and the treatment element may be advanced through the second lumen to the occlusive region. In a preferred embodiment, the treatment element causes at least a portion of the distal portion of the tubular member to assume a nonlinear configuration. The treatment element may be agitated, thereby agitating the distal portion of the tubular member to disrupt or dislodge occlusive material from the occlusive region.

Optionally, a thrombolytic agent and/or other diagnostic or therapeutic agent may be introduced into the occlusive region, e.g., through the second lumen, either before, during, or after advancing the treatment element. In addition or alternatively, a source of vacuum may connected to the second lumen to aspirate material from the target site via the second side port.

In accordance with another aspect of the present invention, an apparatus is provided that includes a tubular member including proximal and distal ends, a distal portion, and a guidewire lumen therein extending from the proximal end to a side port in the distal portion. An expandable member is provided on the tubular member between the side port and the distal end of the tubular member, and a loop defining an aperture extends from the distal end of the tubular member.

During use, a guidewire may be placed through a patient's vasculature to an occlusive region to be treated, and the guidewire may be backloaded through the loop, around the expandable member, and into the lumen. The distal portion of the tubular member may be advanced over the guidewire to the occlusive region. The expandable member on the tubular member may be expanded to at least partially isolate the occlusive region. The guidewire may be removed from the lumen, and a treatment element may be advanced through the lumen into the distal portion.

The occlusive region may be treated using the treatment element. For example, the treatment element may cause at least a portion of the distal portion of the tubular member to assume a nonlinear configuration, and the treatment element may be agitated to disrupt or dislodge occlusive material from the occlusive region, similar to the previous embodiment.

Other objects and features of the present invention will become apparent from consideration of the following description taken in conjunction with the accompanying drawings.

BRIEF DESCRIPTION OF THE DRAWINGS

FIG. 1 is a side view of a preferred embodiment of a catheter including a balloon thereon, in accordance with the present invention.

FIG. 2 is a detail of a distal portion of the catheter of FIG. 1, with a guidewire received therein and the balloon expanded.

FIG. 3 is a cross-sectional view of the catheter of FIG. 1, taken along line 3-3.

DETAILED DESCRIPTION OF THE INVENTION

Figure 4:
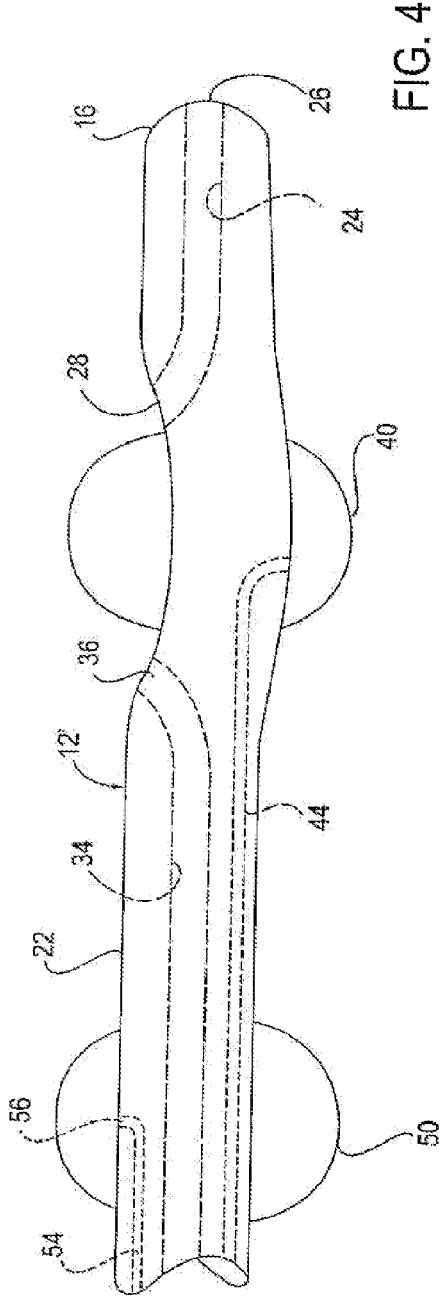
FIG. 4 is a side view of an alternative embodiment of a catheter including a pair of balloons thereon, in accordance with the present invention.

Turning to the drawings, FIGS. 1-3 show a first preferred embodiment of an apparatus 10 for treating an occlusive region within a patient's vasculature, in accordance with the present invention. Generally, the apparatus 10 includes a catheter or other tubular member 12, including a proximal end 14 and a distal end 16 defining a longitudinal axis 18 therebetween, and a balloon 40 on a distal portion 22 of the catheter 12.

The catheter 12 may be a semi-rigid or substantially flexible tubular body formed from conventional materials, such as plastic. The flexibility of the catheter 12 may vary along its length; for example, a proximal portion 20 of the catheter 12 may be relatively stiff, e.g., to facilitate pushing the catheter 12, while the distal portion 22 may be relatively flexible, e.g., to facilitate advancing the distal portion 22 through tortuous anatomy. The catheter 12 may be substantially round in periphery and/or straight in length in a relaxed state, or may be preshaped. In addition or alternatively, the catheter 12 may include an axially asymmetrical, e.g., elliptical or noncircular cross-section at one or more locations along its length. The catheter 12 may terminate in a tapered, rounded, and/or soft distal end 16, which may facilitate substantially atraumatically advancing the catheter 12 through a patient's vasculature.

The distal portion 22 may include a first guidewire lumen 24 therein that includes an end port 26 at or adjacent the distal end 16 and a first side port 28 located proximally of the end port 26. The first lumen 24 may have a relatively short length, e.g., between about three and twenty millimeters (3-20 mm). The catheter 12 may also include a second lumen 34 extending from the proximal end 14 to a second side port 36 located proximally to the first side port 28. One or both of the first and second lumens 24, 34 may include a ramped region 29, 39 therein, which i may facilitate guiding a guidewire 5 (shown in FIG. 2) or other elongate element (not shown) into and/or out of the lumens 24, 34.

The first and second lumens 24, 34 may be sufficiently large to receive the guidewire 5 or other elongate element (not shown) therethrough, e.g., having a diameter of about 0.3-1.5 millimeters (0.014-0.050 inch). Preferably, the second lumen 34 is larger than the first lumen 24 such that the second lumen 34 may be used for multiple purposes, as explained further below. For example, the first lumen 24 may have a diameter of about 0.3-1.0 millimeter, while the second lumen 34 may have a diameter of about 0.8-1.5 millimeters.

The balloon 40 may be provided on the distal portion 22 of the catheter 12, preferably between the first and second side ports 28, 36. The balloon 40 may be formed from elastomeric materials, e.g., silicone, latex, urethane, isoprene, chronoprene, and the like, that is attached to an outer surface of the catheter 12, e.g., using an adhesive, sonic welding, balloon wrapping, and the like. The balloon 40 may be an annular shaped body, or may simply be an expandable skin attached to the catheter 12, e.g., at its proximal end distal ends 41, 42. Preferably, the balloon 40 is substantially compliant such that the balloon 40 may expand to sealingly engage a wall of a blood vessel (not shown) without applying a substantial radial force against the wall, i.e., without substantially dilating the wall. In addition, the balloon material may have a sufficiently low coefficient of friction such that the balloon 40 may slidably engage a wall of a vessel, as described further below. Alternatively, other expandable members, e.g., a mechanically expandable member (not shown), may be provided instead of the balloon 40.

The catheter 12 may include a third lumen 44 that extends from the proximal end 14 to an outlet port 46 on the portion of the catheter 12 over which the balloon 40 is secured. In an in exemplary embodiment, shown in FIG. 3, the second lumen 34 may extend through the catheter 12, thereby defining a side wall within which the third lumen 44 may be provided. Alternatively, the lumens 34, 44 may be provided in other side-by-side or concentric arrangements, as is known in the art. A source of fluid, e.g., saline (not shown), may be coupled to an inlet port 48 on the proximal end 12, thereby communicating with an interior of the balloon 40 to inflate the balloon 40. Similarly, if desired, a source of vacuum (also not shown) may be coupled to the inlet port 48 to deflate the balloon 40.

One or more seals or valves (not shown) may be provided on the proximal end 14 of the catheter 12, e.g., to seal the second and/or third lumens 34, 44, as is well known in the art. For example, a hemostatic valve (not shown) may be provided, e.g., to seal the second lumen 34 from proximal fluid flow, while allowing devices, e.g., a guidewire 5, to be introduced into the second lumen 34. In addition, a stopcock or other valve (not shown) may be provided at the inlet port 48 to seal the third lumen 44. Thus, the valve may be opened to allow fluid to be introduced into the third lumen 44, and may be closed to maintain the fluid within the third lumen 44, e.g., to inflate the balloon 40.

Optionally, as shown in FIG. 4, the catheter 12' may include a second or proximal balloon 50 or other expandable member on the distal portion 22' proximal to the balloon 40 and/or the second side port 36. The second balloon 50 may be located between about one a sixty centimeters (1-60 cm) from the first or distal balloon 40. The catheter 12' may include a fourth lumen 54 extending from the proximal end 14 (not shown) to an outlet port 56 communicating with an interior of the balloon 50. Alternatively, a single inflation lumen (not shown) may communicate with the interior of the first and second balloons 50, which may be used to inflate and/or deflate the first and second balloons 40, 50 substantially simultaneously.

Figure 5:
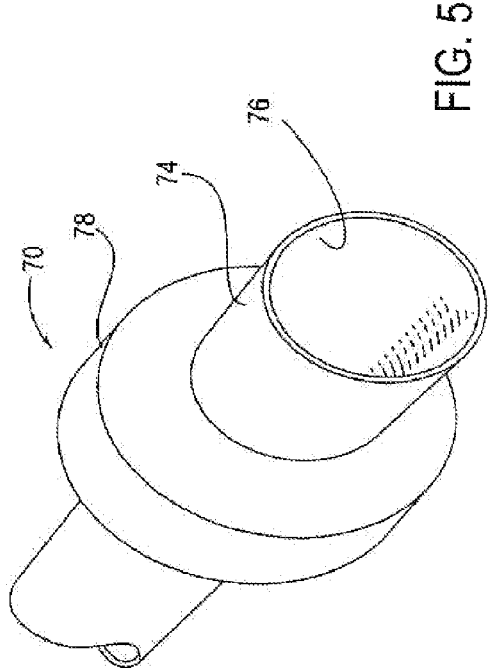
FIG. 5 is a perspective view of a distal end of a balloon catheter that may be used in conjunction with the catheter of FIG. 1.

Alternatively, if the catheter 12 does not include a second balloon 50 (as shown in FIG. 4), a separate balloon catheter 70 may be used to facilitate isolating a region of a blood vessel, such as that shown in FIG. 5. Generally, the balloon catheter 70 is a semi-rigid or flexible tubular body including a lumen 76 extending between its proximal end (not shown) and its distal end 74. Preferably, the lumen 76 is sufficiently large such that at least a portion of the catheter 12 (not shown, see FIG. 1) may be received therein and/or the balloon catheter 70 may be slidably received over the catheter 12. A balloon 78 or other expandable member may be provided on or adjacent the distal end 74, e.g., a compliant balloon, similar to that provided on the catheter 12. If the balloon 78 is disposed proximally to the distal end 74 of the balloon catheter 70, the distal end 74 may be tapered, rounded, and/or soft to facilitate substantially atraumatically advancing the catheter 70 through a patient's vasculature. The balloon catheter 70 may also include an inflation lumen (not shown) that communicates with an interior of the balloon 78 and extends to the proximal end of the balloon catheter 70.

Figure 6:
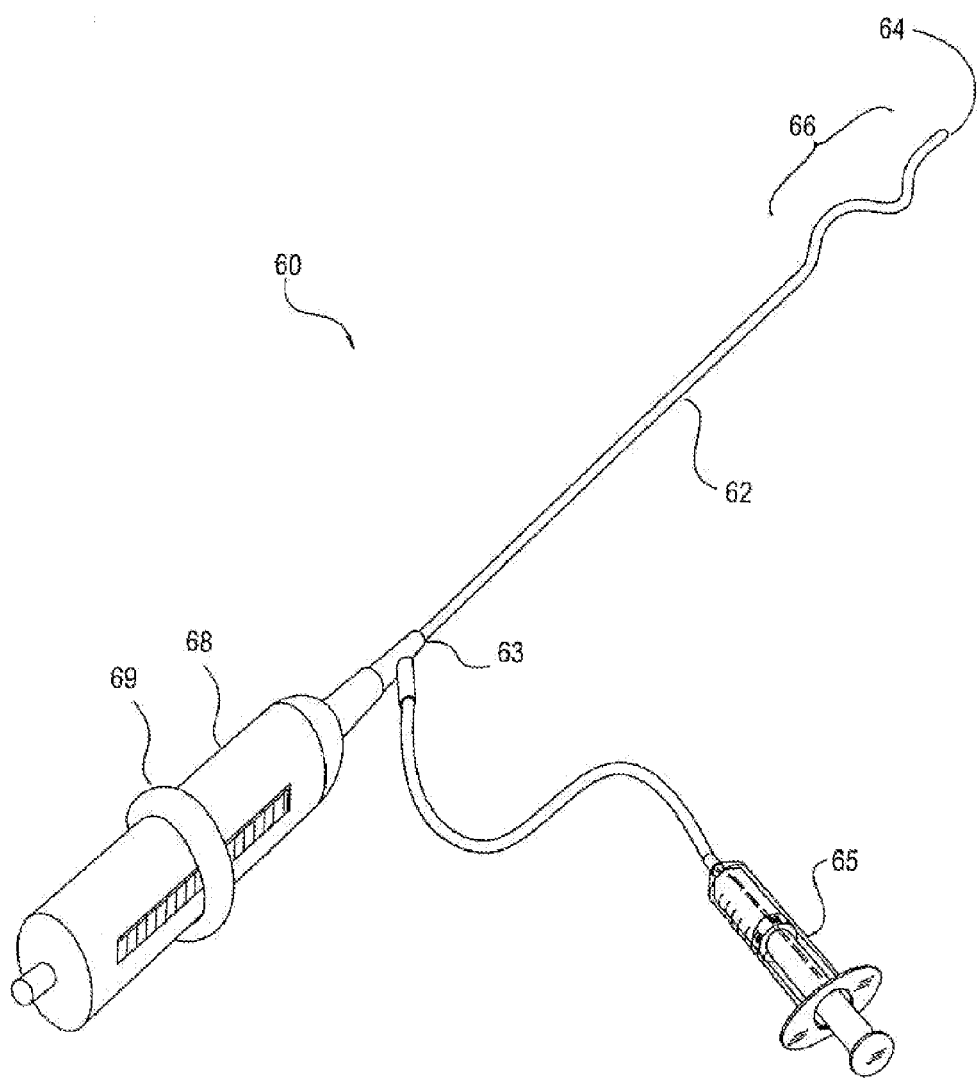
FIG. 6 is a perspective view of an agitator that may be used in conjunction with a catheter, in accordance with the present invention.

Turning to FIG. 6, in a preferred embodiment, the apparatus (or the apparatus 10' of FIG. 4) may be used in conjunction with an agitator 60 for disrupting and/or dislodging occlusive material, e.g. thrombus, from a wall of a blood vessel (not shown). In addition or alternatively, the apparatus 10 may be used in conjunction with other endovascular devices to perform a procedure at a target region within a patient's vasculature. For example, a source of thrombolytic agent or other fluid, and/or a source of aspiration (not shown) may be connected to the proximal end 14 of the catheter 12.

Generally, the agitator 60 includes an elongate catheter or agitator element 62, e.g., a semi-rigid or flexible tube or wire, including a proximal end 63 and a distal end 64. The agitator element 62 includes a nonlinear portion 66, e.g., having a sinusoidal or other axially asymmetrical shape. Alternatively, the nonlinear portion 66 may have other two-dimensional or three dimensional geometries (not shown). The agitator element 62 has a cross-section, e.g., diameter, such that it may be inserted into the second lumen 34 of the catheter 12 (not shown, see FIG. 1). In addition, the agitator element 62 has a length such that the nonlinear portion 66 may be disposed in the distal portion 22 of the catheter 12 proximal to the balloon 40 when the agitator element 62 is fully received in the second lumen 34.

Preferably, the nonlinear portion 66 of the agitator element 62 is formed from a resilient material that is biased to the nonlinear shape when free from any constraint, e.g., a nickel titanium alloy ("Nitinol"). The distal portion 22 of the catheter 12 is sufficiently flexible such that, when the nonlinear portion 66 is inserted into the distal portion 22, the distal portion 22 assumes a nonlinear shape similar to the nonlinear portion 22, as explained further below.

The agitator 60 also includes a handle or hub 68 on the proximal end 63 that may be used to manipulate the agitator 60 and/or move the nonlinear portion 66. For example, a collar 69 on the handle 68 may be used to displace the agitator element 62, and, consequently, the nonlinear portion 66, axially (proximally and/or distally). In addition or alternatively, the handle 68 may include a motor (not shown) therein for oscillating the agitator element 62, e.g., axially and/or rotationally about the longitudinal axis 18 (i.e., relative to the handle 68). The motor may include its own power source, e.g., one or more batteries (not shown), within the handle 68 for powering the motor. Alternatively, a cable (not shown) may extend from the handle 68 that may be coupled to a power supply (also not shown).

The motor may include an output shaft (not shown) that may be directly or indirectly coupled to the agitator element 62. Thus, when the motor is operated, the agitator element 62 may be displaced axially and/or rotated about the longitudinal axis 18, as explained further below. Alternatively, the handle 68 may include a drive element, e.g., a drive shaft, hub, and/or socket (not shown), extending from the handle 68 that is coupled to the agitator element 62. An external motor drive unit (not shown) may be connected to the drive element to oscillate the agitator element 62. Additional information on an agitator that may be used in conjunction with the present invention is described in PCT publication WO 01/54754, published Aug. 8, 2001, assigned to the assignee of the present application. The disclosures of this reference and any others cited therein are expressly incorporated herein by reference.

Optionally, the agitator element 62 may be hollow, i.e., including a lumen (not shown) that extends from the proximal end 63 to the distal end 64. The distal end 64 may include an outlet (not shown), and/or the nonlinear portion 66 may include one or more side ports (also not shown). If so, a source of fluid 65 may be connected to the proximal end 63 for delivering fluid, e.g., a thrombolytic agent, and the like, through the outlet and/or side ports in the agitator element 62.

Turning to FIGS. 7A-7E, during use of the apparatus 10, a target site 92 may be selected for treatment, e.g., an occlusive region within a blood vessel 90 of a patient. The target site 92 may be a region of an artery or vein, such as a coronary, carotid, cerebral, or other peripheral artery, within which thrombus, plaque, and/or other occlusive material 94 has been deposited. A guidewire 5 may be advanced into the target site 92 using conventional methods. For example, an introducer (not shown) may provide access from a percutaneous entry site into the patient's vasculature, e.g., into a peripheral vessel, such as a femoral or carotid artery. The guidewire 5 may be advanced through the introducer and the patient's vasculature until a distal end 6 of the guidewire 5 is positioned across the target site 92. Thus, a proximal end (not shown) of the guidewire may remain outside the percutaneous entry site, thereby allowing one or more therapeutic and/or diagnostic devices to be advanced over the guidewire 5 to the target site 92.

Turning to FIG. 2, before the apparatus 10 may be advanced over the guidewire 5, the proximal end of the guidewire 5 is backloaded through the first and second lumens 24, 34 of the catheter 12. First, the guidewire 5 is inserted into the end port 28, and advanced through the first lumen 24 until it exits the first side port 26. The guidewire 5 is then inserted into the second side port 38, and advanced through the second lumen 34 until the guidewire 5 exits at the proximal end 14 of the catheter 12. Thus, the guidewire 5 may pass along an exterior of the distal portion 22 of the catheter 12 over the balloon 40 (although the balloon 40 is preferably substantially collapsed against the distal portion 22 initially, and not expanded as shown in FIG. 2). Alternatively, the guidewire 5 may remain outside the second lumen 34, e.g., passing proximally along the exterior of the catheter 12 to the proximal end 14 (not shown).

The distal portion 22 of the catheter 12 may be introduced into the patient's vasculature over the guidewire 5. Because the end port 28 of the first lumen 24 is disposed at or near the distal end 16 of the catheter 12, the distal end 16 of the catheter 12 generally tracks the guidewire 55 closely. This may substantially minimize the distal end 16 skiing along the wall of vessels through which the catheter 12 is advanced, particularly when the catheter 12 is advanced through tortuous anatomy. Thus, the risk of dislodging embolic material from the wall and/or otherwise damaging or puncturing the wall of the vessels may be substantially reduced.

Figure 7A:
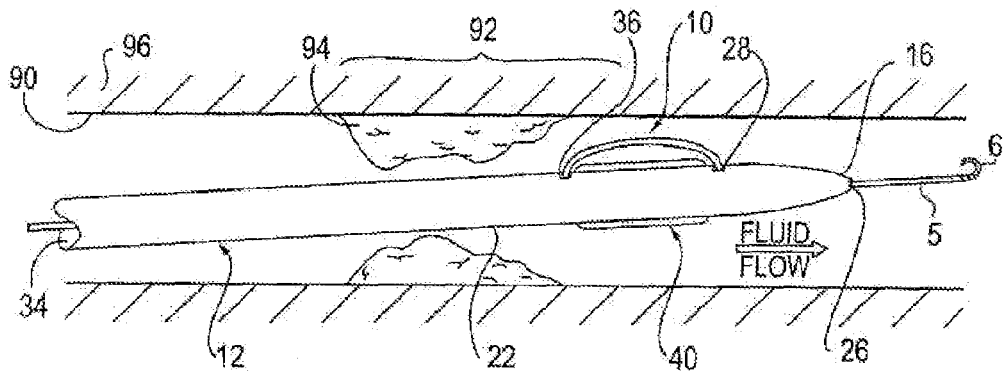
FIGS. 7A-7E are cross-sectional views of a blood vessel, showing a method for treating an occlusive region, in accordance with the present invention.

Turning to FIG. 7A, the distal portion 22 of the catheter 12 may be advanced into the target site 92, e.g., such that the balloon 40 is disposed distally beyond the occlusive material 94 intended to be removed or otherwise treated. The distal portion 22 of the catheter 12 may include-one or more radiopaque markers and the like (not shown) thereon, which may be observed, e.g., using fluoroscopy or other external imaging, to facilitate positioning the distal portion 22.

Figure 7B:
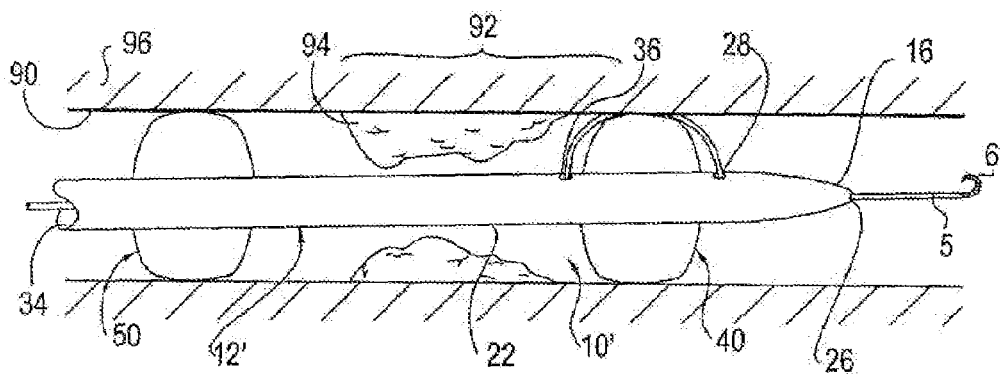
Figure 7C:
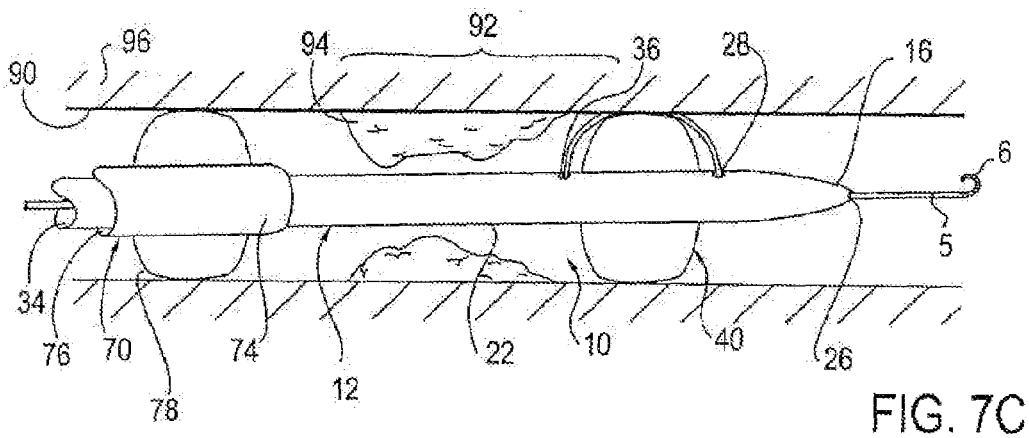

As shown in FIGS. 7B and 7C, once the distal portion 22 is properly positioned within the target site 92, the balloon 40 may be inflated or otherwise expanded until it contacts the wall 96 of the vessel 90. This may cause the guidewire 5 to slide within one or both of the first and second lumens 24, 34 to provide slack and allow the guidewire to expand laterally as the balloon 40 expands, as shown in FIG. 7B. Because of the elasticity and/or compliant nature of the balloon material, the balloon 40 may engage the guidewire 5 and/or the wall 96 to substantially seal the vessel 90 from fluid flow therethrough without applying substantial radial force outwardly against the wall 96. Thus, once the balloon 40 is inflated, it may at least partially isolate the target site 92 from other regions of the vessel 90. The balloon 40 may be particularly important when fluid naturally flows within the vessel 90 in an antegrade direction relative to the catheter 12 (i.e., the direction shown in FIG. 7A).

In an alternative embodiment, the guidewire 5 may be withdrawn from the catheter 12 before the balloon 40 is inflated, i.e., by pulling the guidewire 5 proximally through the first and second lumens 24, 34. The balloon 40 may then be inflated to substantially engage the wall 96 of the vessel 90.

If, as shown in FIG. 7B, the catheter 12' includes a proximal balloon 50, the proximal balloon 50 may be inflated before, after, or simultaneously with the distal balloon 40. Preferably, the proximal balloon 50 is located a predetermined distance from the distal balloon 40 that is sufficiently long such that the proximal balloon 50 is located proximally to the occlusive material 94 when the distal balloon 40 is located distally to the occlusive material 94. With both balloons 40, 50 inflated, the target site 92 may be substantially isolated from the rest of the vessel 90.

Alternatively, as shown in FIG. 7C, if the catheter 12 does not include a proximal balloon, a separate balloon catheter 70 may be advanced over the catheter 12 until a balloon 78 carried by the balloon catheter 70 is positioned proximally to the occlusive material 94. The balloon 78 may then be inflated to substantially isolate the target site 92. One advantage of using a separate balloon catheter 70 is that the relative distance between the proximal and distal balloons 50, 40 may be adjusted by the user based upon the length of the target region encountered. However, using a separate balloon catheter 70 may increase the overall cross-sectional profile of the apparatus, as compared to using a catheter 12' with a proximal balloon 50.

Figure 7D:
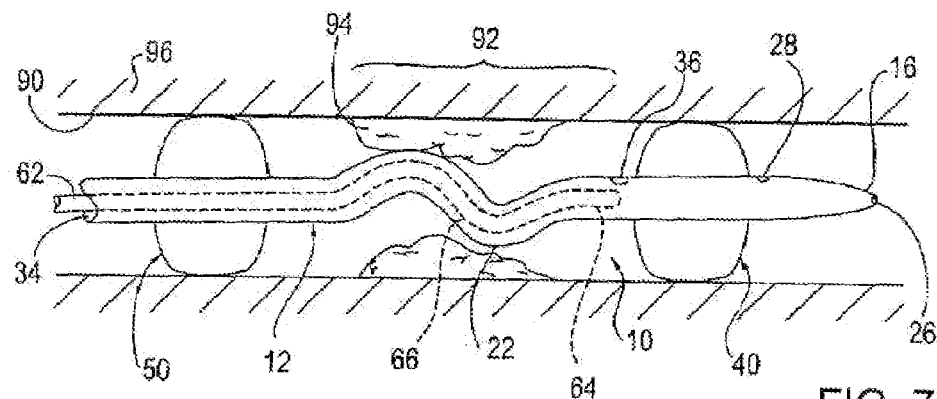
Figure 7E:
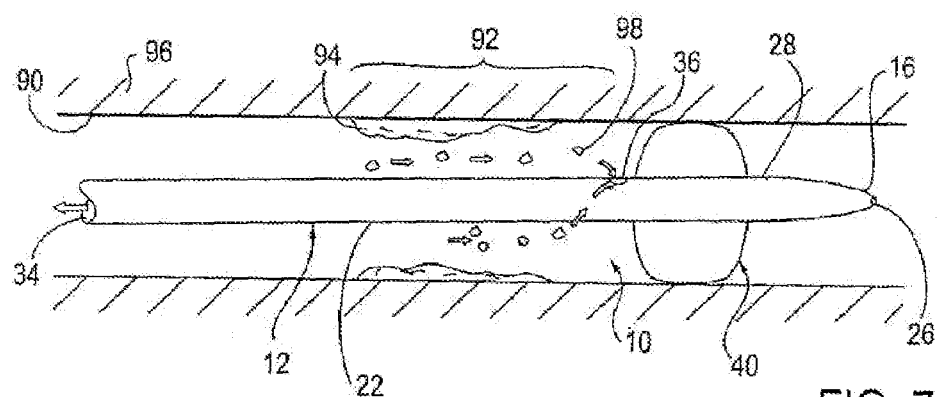

Turning to FIG. 7D, with the target site 92 substantially isolated, the guidewire 5 may be withdrawn from the catheter 12, i.e., pulled proximally through the first and second lumens 24, 34 (unless already withdrawn, as explained above). A treatment element may be advanced into the target site 92 in cooperation with the tubular member. For example, the agitator element 62 from the agitator 60 (not shown, see FIG. 6) may be advanced into the second lumen 34 from the proximal end 14 (not shown) of the catheter 12. As the nonlinear portion 66 (shown in phantom) enters the distal portion 22 of the catheter 12, it may cause the distal portion 22 to assume a nonlinear configuration, as shown in FIG. 7D.

The agitator 60 may be secured or otherwise maintained relative to the proximal end 14 of the catheter 12, e.g., by cooperating connectors (not shown) on the proximal end 14 of the catheter 12. The agitator element 62 may be activated to treat the target region, e.g., by turning on a motor (not shown) to move the agitator element 62. Preferably, the nonlinear portion 66 of the agitator 60 is agitated, e.g., oscillated axially, linearly, and/or rotationally. Consequently, the distal portion 22 of the catheter 12 is agitated within the target site 92 to disrupt and/or dislodge the occlusive material 94 from the wall 96 of the vessel 90.

To enhance the action of this agitation, a thrombolytic agent or other fluid may be introduced into the target site 92. For example, a thrombolytic agent may be introduced through the second lumen 34 and out the second side port 36 into the target site 92. If the second lumen 34 is larger than the agitator element 62, the thrombolytic agent may be introduced through the second lumen 34 around the agitator element 62. Alternatively, the thrombolytic agent may be introduced through the second lumen 34 before the agitator element 62 is inserted into the second lumen 34. In a further alternative, the agitator element 62 may include one or more outlets (not shown) in the distal end 64 and/or nonlinear portion 66 through which the thrombolytic agent i may be introduced. In yet a further alternative, if a separate balloon catheter 70 is used (as shown in FIG. 7C), the thrombolytic agent may be introduced through the lumen 76 around the catheter 12 and into the target site 92 (or another lumen (not shown) in the balloon catheter 70).

After a desired time, the agitator 60 may be stopped, e.g., after sufficient occlusive material 98 has been disrupted and/or dislodged from the wall 96 of the vessel 90. Because of the activity of the agitator 60 and/or the thrombolytic agent, the loose occlusive material 98 may be dissolved or otherwise broken down sufficiently such that it may be harmless to the patient being treated.

Preferably, however; the loose occlusive material 98 is aspirated from the target site 92 For example, the agitator element 62 may be removed from the second lumen 34, and a source of aspiration (not shown) may be connected to the proximal end 14 of the catheter 12 that communicates with the second lumen 34. Thus, a vacuum may be created at the second side port 36 to aspirate occlusive material from the occlusive region. Preferably, the second balloon 50 (or the balloon 78 on the balloon catheter 70) may be deflated before aspirating the target site 92 in order to allow fluid from the vessel 90 to flow into the target site 92 as the occlusive material 98 and surrounding fluid are evacuated from the target site 92.

Preferably, the second side port 36 and/or the second lumen 34 are sufficiently large to allow relatively large pieces of occlusive material 98 to be drawn into the second side port 36 and/or evacuated through the second lumen 34. Although a single side port 36 is shown, it may be possible to provide additional side ports (not shown) in the distal portion 22 of the catheter 12 that communicate with the second lumen 34 for delivering a thrombolytic agent and/or aspirating occlusive material from the target site 92.

Alternatively, if the balloon catheter 70 is used (as shown in FIG. 7C), the occlusive material 98 may be aspirated through the lumen 76 or another lumen (not shown) in the balloon catheter 70. In a further alternative, with the balloon 40 expanded, the catheter 12 may be pulled proximally. Because of its compliant, low-friction nature, the balloon 40 may slidably engage the wall 96 of the vessel 90, thereby directing occlusive material proximally, e.g., into the lumen 76 of the balloon catheter 70.

Once the occlusive material 98 has been aspirated, the balloon 40 may be collapsed, and the apparatus 10 may be withdrawn from the target site 92. Optionally, the apparatus 10 may be moved to another location (not shown), e.g., a target site adjacent the target site 92, and the process may be repeated. Thus, although a single region of occlusive material 94 is shown in FIGS. 7A-7E, it will be appreciated that a target site may be divided into segments, and the method described below may be repeated after moving the apparatus 10 into different segments of the target site.

If desired, a guidewire (not shown) may be reintroduced into the second lumen 34 to facilitate directing the catheter 12 to another location and/or for tracking other devices over the guidewire to the distal portion 22 of the catheter 12.

One advantage of an apparatus in accordance with the present invention is that a separate guidewire lumen is not required in the catheter 12. Instead, a single lumen may be used for a guidewire, as well as for introducing a treatment element, such as the agitator element, into the target site. This may substantially reduce the cross-sectional profile of the catheter 12, thereby allowing the catheter 12 to be advanced into smaller vessels and/or into more occluded regions. Further, separate infusion and/or aspiration lumens are also not necessary. The same lumen may also be used to aspirate loose particulate in the treatment site, which may further reduce the profile. In addition, with a single lumen being used for multiple functions, it may be unnecessary to introduce a separate aspiration catheter into the target site to aspirate loose particulate within the target site. Such a large profile device may risk damaging the vessel or dislodging embolic material as it is advanced over the catheter to the target site.

Figure 8:
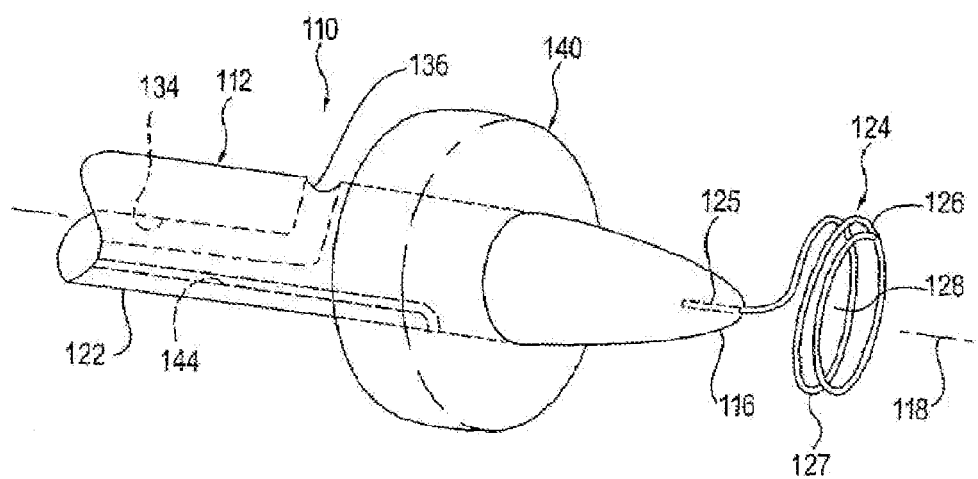
FIG. 8 is a side view of an alternative embodiment of a catheter, in accordance with the present invention.

Turning to FIG. 8, an alternative embodiment of an apparatus 110 is shown that includes a catheter 112, including a proximal end (not shown) and a distal end 116 defining a longitudinal axis 118 therebetween, and a distal portion 122. The catheter 112 may include a first lumen 134 extending from the proximal end to a side port 136 located on the distal portion 122. A balloon 140 may be provided on the distal portion 122 between the side port 136 and the distal end 116 of the catheter 112. The catheter 112 may include a second lumen 144 that communicates with an interior of the balloon 140, all similar to the previous embodiment. Optionally, the catheter 112 may include a second balloon (not shown) located proximally to the first side port 136.

Unlike the previous embodiment, a helical element or loop 124 extends from the distal end 116 of the catheter 112, e.g., generally parallel to the longitudinal axis 118. The helical element 124 may be an elongate wire having a first end 125 bonded or otherwise secured to the distal end 116 of the catheter 112. For example, the first end 125 may be secured using an adhesive, by melting the distal end 116 around the first end 125, and/or by heating the first end 125 and forcing it into the distal end 116. A second end 126 of the helical element 124 is wound about an axis 118 into one or more turns 127 defining an aperture 128 therethrough. The turns 127 may have spaces between them or adjacent turns may substantially abut one another. Preferably, the helical element 124 is formed from a resilient and/or semi-rigid material that may be formed into the helical shape, yet may be deflected in order to accommodate advancing the helical element 124 through a patient's vasculature.

In a further alternative, an enclosed loop (not shown) may be provided on the distal end 116 of the catheter 112, instead of the helical element 124. Such a loop is disclosed in U.S. Pat. No. 4,824,435, the disclosure of which is expressly incorporated herein by reference.

Similar to the previous embodiment; the apparatus 110 may be used to treat an occlusive region within a blood vessel or other body lumen (not shown). A guidewire (not shown) may be backloaded through the aperture 128 defined by the helical element 124, into the side port 136, and through the first lumen 134 before advancing the catheter 112 over the guidewire and into a patient's vasculature. Once a target site is achieved, the guidewire may be removed from the first lumen 134, i.e., by pulling the guidewire through the helical element 124 and the first lumen 134. The balloon 140 may be expanded to at least partially isolate the target site; and, optionally, a second or proximal balloon (not shown) may be expanded to substantially isolate the target site. A treatment element, such as the agitator 60 shown in FIG. 6, may be advanced into the target site, e.g., through the first lumen 134, and used to treat the target site, as explained above.

In further alternative embodiments, other diagnostic or therapeutic devices may be provided on or otherwise carried by the catheters described above. For example, the first and second side ports (and the compliant balloon between them) may be located a predetermined distance from the distal tip of the catheter. Another device, such as an angioplasty balloon (an inelastic or other noncompliant expandable balloon), a filter, and the like, may be mounted or otherwise provided on the catheter at a location distal to the compliant balloon. In yet further alternatives, a plurality of substantially compliant balloons (not shown) may be provided on the catheter between the first and second side ports.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method for treating an occlusive region of a patient's vasculature using a tubular member comprising proximal and distal ends, and a distal portion comprising a first lumen therein, the first lumen comprising an end port at or adjacent to the distal end and a first side port located proximally to the end port, the tubular member further comprising a second lumen extending from the proximal end to a second side port located proximally to the first side port, and an expandable member between the first and second side ports, the method comprising:

placing a guidewire through a patient's vasculature to an occlusive region to be treated;

backloading the guidewire through the first lumen, around the expandable member, and through the second lumen;

advancing the distal portion of the tubular member over the guidewire to the occlusive region;

expanding the expandable member on the tubular member to at least partially isolate the occlusive region;

advancing a treatment element into the occlusive region in cooperation with the tubular member; and treating the occlusive region.

2. The method of claim 1, wherein the step of advancing a treatment element comprises:

removing the guidewire from the second lumen; and advancing the treatment element through the second lumen to the occlusive region.

3. The method of claim 2, wherein the treatment element causes at least a portion of the distal portion of the tubular member to assume a nonlinear configuration.

4. The method of claim 3, wherein the treating step comprises agitating the treatment element to disrupt or dislodge occlusive material from the occlusive region.

5. The method of claim 1, wherein the treating step comprises introducing a therapeutic or diagnostic agent into the occlusive region.

6. The method of claim 5, wherein the therapeutic or diagnostic agent comprises a thrombolytic agent.

7. The method of claim 3, wherein the treating step further comprises creating a vacuum at the second side port to aspirate occlusive material from the occlusive region.

8. The method of claim 7, wherein the treatment element is removed from the second lumen before creating a vacuum.

9. The method of claim 1, wherein the expandable member comprises a distal expandable member, and wherein the method further comprises:

expanding a proximal expandable member to isolate at least a portion of the occlusive region.

10. The method of claim 9, wherein the proximal expandable member is disposed on the tubular member at a location proximal to the second side port.

11. The method of claim 9, wherein the proximal expandable member is carried on a distal portion of an elongate member advanced to the occlusive region.

12. The method of claim 11, wherein the elongate member comprises a balloon catheter that is advanced over the tubular member to the occlusive region.

13. The method of claim 1, further comprising removing the guidewire from the distal portion of the elongate member before expanding the expandable member.

14. A method for treating an occlusive region of a patient's vasculature using a tubular member comprising proximal and distal ends, a lumen therein extending from the proximal end to a side port in the distal portion, an expandable member on the distal portion between the side port and the distal end, and a loop on the distal end, the method comprising:

placing a guidewire through a patient's vasculature to an occlusive region to be treated;

backloading the guidewire through the loop, around the expandable member, and through the lumen;

advancing the distal portion of the tubular member over the guidewire to the occlusive region;

expanding the expandable member on the tubular member to at least partially isolate the occlusive region;

removing the guidewire from the lumen;

advancing a treatment element through the lumen into the distal portion; and treating the occlusive region using the treatment element.

15. The method of claim 14, wherein the treatment element causes at least a portion of the distal portion of the tubular member to assume a nonlinear configuration.

16. The method of claim 14, wherein the treating step comprises agitating the treatment element to disrupt or dislodge occlusive material from the occlusive region.

17. The method of claim 16, wherein the treating step further comprises introducing a thrombolytic agent into the occlusive region.

18. The method of claim 16, wherein the treating step further comprises creating a vacuum at the second side port to aspirate occlusive material from the occlusive region.

19. The method of claim 14, wherein the guidewire is removed from the lumen before expanding the expandable member.

\* \* \* \* \*